US009011902B2

(12) United States Patent
Di Schiena (10) Patent No.: US 9,011,902 B2
(45) Date of Patent: Apr. 21, 2015

(54) COMPOSITION FOR VAGINAL USE (75) Inventor: Michele Di Schiena, Robecco Sul Naviglio (IT)

(73) Assignee: Polichem SA, Luxembourg (LU)

( * ) Notice: Subject to any disclaimer, the term of this patent is extended or adjusted under 35 U.S.C. 154(b) by 490 days.

(21) Appl. No.: 12/220,160

(22) Filed: Jul. 22, 2008

(65) Prior Publication Data
US 2009/0035361 A1    Feb. 5, 2009

Related U.S. Application Data (63) Continuation-in-part of application No. PCT/EP2006/069643, filed on Dec. 13, 2006.

(30) Foreign Application Priority Data

Jan. 25, 2006  (IT) ............................. MI2006A0122

(51) Int. Cl.
*A61K 9/127* (2006.01)
*A61K 36/185* (2006.01)
*A61K 9/00* (2006.01)

(52) U.S. Cl.
CPC ............. *A61K 36/185* (2013.01); *A61K 9/0034* (2013.01)

(58) Field of Classification Search
None
See application file for complete search history.

(56) References Cited

U.S. PATENT DOCUMENTS

| 2003/0124204 A1* | 7/2003 | Sweet ........................... 424/725 |
| 2005/0019438 A1* | 1/2005 | Bourges-Sevenier et al. ........................ 424/778 |
| 2005/0042318 A1 | 2/2005 | Erdelmeier |
| 2006/0127412 A1 | 6/2006 | Kakuo |
| 2008/0102114 A1* | 5/2008 | Koritala et al. ............... 424/456 |

FOREIGN PATENT DOCUMENTS

| DE | 20320103 | 7/2004 |
| JP | 2004537804 | 12/2004 |
| JP | 2005343873 | 12/2008 |
| WO | WO 02/076410 | 10/2002 |
| WO | WO 02/085393 | 10/2002 |
| WO | WO 2007/085327 | 8/2007 |
| WO | WO 2007085327 | * 8/2007 |

OTHER PUBLICATIONS

Giancarlo Morali et al. ( Drug research 56, No. 3, 230-238). 2006.*
Castelo-Branco, et al. Management of post-menopausal vaginal atrophy and atrophic vaginitis:. Maturita, Elsevier Science Publishers Ireland Ltd. vol. 52, pp. 46-52, 2005.
Pavelic, et al. International Journal of Pharmaceutics, vol. 301, pp. 140-148, 2005.
Yasukawa, et al. Phytotherapy Research, vol. 7, pp. 185-189, 1993.
Morali, et al. Arzneimittel-Forschung, vol. 56, pp. 230-238, 2006.
International Search Report for International Application No. PCT/EP2006/069643, Apr. 23, 2007.
Written Opinion of the International Searching Authority for International Application No. PCT/EP2006/069643, Apr. 23, 2007.
Medline Citation of Morali, et al., accessed online at the National Center for Biotechnology Information, Sep. 3, 2010.
Liu. J., et al. "Evaluation of Estrogenic Activity of Plant Extracts for the Potential Treatment of Menopausal Symptoms", J. Agric. Food Chem. 2001, 49, 2472-2479.
Proserpio, et al. Elementi Di Fitocosmesi, vol. 1, SEPEM, Milano IT,. 1982., and English launguage translation of excerpt.

* cited by examiner

*Primary Examiner* — Snigdha Maewall
(74) *Attorney, Agent, or Firm* — Hueschen and Sage (57) ABSTRACT

Compositions for vaginal use comprising lupulus (*Humulus lupulus*) and an excipient base suitable for application in the vaginal and/or vulvar region, for the treatment of vaginal dryness (atrophic vaginitis) and of the disorders correlated thereto, pruritus, burning sensation, dryness, dyspareunia; they are also particularly useful for delaying and attenuating the changes in the physiological trophism of the vulvar and vaginal tissue and mucosa.

16 Claims, 5 Drawing Sheets

Figure 1. Vaginal dryness (visual analog scale, VAS) in post-menopausal women treated with the product in a study for 12 weeks. (Visit 1= 8 days; Visit 2= 28 days; Visit 3= 56 days; Visit 4= 84 days)

Figure 2. Subjective symptoms in post-menopausal women treated with the product in a study for 12 weeks. (Visit 1= 8 days; Visit 2= 28 days; Visit 3= 56 days; Visit 4= 84 days) A: number of patients per severity of the symptom; B-D: average severity ± 2 SD.

A

| | | Itching | Burning | Dyspareunia |
|---|---|---|---|---|
| Baseline | absent | 0 | 0 | 0 |
| | mild | 0 | 12 | 22 |
| | moderate | 16 | 24 | 52 |
| | severe | 70 | 50 | 12 |
| Visit 1 | absent | 0 | 10 | 18 |
| | mild | 13 | 29 | 35 |
| | moderate | 69 | 45 | 32 |
| | severe | 4 | 2 | 1 |
| Visit 2 | absent | 0 | 12 | 28 |
| | mild | 82 | 70 | 54 |
| | moderate | 4 | 4 | 4 |
| | severe | 0 | 0 | 0 |
| Visit 3 | absent | 79 | 80 | 77 |
| | mild | 6 | 6 | 9 |
| | moderate | 1 | 0 | 0 |
| | severe | 0 | 0 | 0 |
| Visit 4 | absent | 84 | 84 | 85 |
| | mild | 2 | 2 | 1 |
| | moderate | 0 | 0 | 0 |
| | severe | 0 | 0 | 0 |

B

PRURITUS

C

BURNING SENSATION

D

DYSPAREUNIA

Figure 3. Objective examination in post-menopausal women treated with the product in a study for 12 weeks. (Visit 1= 8 days; Visit 2= 28 days; Visit 3= 56 days; Visit 4= 84 days) A-B: average severity ± 2 SD. C-D: number of patients per presence of the symptom.

Inflammation/oedema of vaginal mucosa

Eruption of the vaginal mucosa

Disepithelialisation

Vulvo-vaginal abrasion

Figure 4 - percent cell proliferation, normalised to the medium: 1st experiment (n=8);

Figure 5 - percent cell proliferation, normalised to the medium: 2nd experiment (n=8)

Figure 6 - percent cell proliferation, normalised to the medium: 3<sup>rd</sup> experiment (n=20)

COMPOSITION FOR VAGINAL USE

The subject of the invention is compositions for vaginal use containing lupulus (*Humulus lupulus*) as an active ingredient, for the preparation of a medicinal speciality, or of a medical device, or of a cosmetic, or of a sanitary product, for application to the vaginal and/or vulvar region, useful for the treatment of vaginal dryness (atrophic vaginitis) and of the disorders correlated thereto, pruritus, burning sensation, dryness, dyspareunia; they are further particularly useful for delaying and attenuating the changes in the physiological trophism of the vulvar and vaginal tissue and mucosa.

Vaginal dryness (atrophic vaginitis) may arise from various causes, including pathological causes, but it is more often a paraphysiological condition very common in the menopause, caused by the gradual reduction of the oestrogens circulating in the blood (hypoestrogenaemia); this physiological reduction of the oestrogens involves the reduction of cellular glycogen and the consequent alteration of the vaginal pH and of the saprophyte bacterial flora.

This condition involves characteristic symptoms affecting the genital tissues and mucosa such as, for example, burning sensation, irritation, dryness; it may further evolve into actual pathologies such as, for example, mycotic infections (*Candida*); vaginal dryness may further render sexual relations particularly difficult (dyspareunia).

It is therefore obvious that vaginal dryness may have a negative effect on the quality of a woman's life from the physical, emotional and psychological point of view.

Therapy with synthesised oestrogens (e.g. promestriene) by the topical route, is known in the art for the treatment of atrophic vaginitis, but its use is not devoid of undesirable side effects, even serious ones such as, for example, water retention and the stimulation of tumoral receptors such as, for example, the mammary tumour receptor.

Moreover, the synthesised oestrogens are prohibited for cosmetic or in any case non-pharmaceutical use precisely because of the severe side effects.

Lupulus is a plant widely distributed in nature, its best known use being for the production of beer, to which it imparts the classic bitter flavour.

The phytocomplex of the plant contains fluoroglucinic compounds: 3-isopentenylfluoroisovalerophenone, humulone, adhumulone, cohumulone, lupulone, colupulone, adlupulone; flavonoids and chalcones: 6-isopentenylnaringenine, xanthohumol, isoxanthohumol, quercetin, kaemferol and glucosides; essential oil containing: alpha-cariophyllene, mircene, beta-cariophyllene, farnesene, linalool, 2-methylbut-3-ene-2-ol, 3-methylbut-2-ene-1-al, 2,3,5-trithiohexane, 2-methylpropanoic acid, etc.; polyphenols (M. Rossi—Mother Tinctures in phytotherapy—Studio Editions).

The phytocomplex of the plant is characterised by interesting, distinctive properties such as, for example: it inhibits the growth of bacteria and fungi (3-isopentenylfluoroisovalerophenone, bitter acids etc.); it has a protective effect on the blood capillaries (polyphenols, etc.); has antiandrogenic properties (M. Rossi, loc.cit.); it stimulates, revitalises and normalises the tone and turgidity of the skin and of the cutaneous adnexa (phytosterols, etc.).

In phytotherapy, lupulus and its extracts are used orally in sleep disorders and in spasmophilias, in particular in the menopause; it is used topically in mycotic dermatitis.

Also in the cosmetic field it is known to use lupulus and its extracts as a phytocosmetic functional substance having a stimulating, tonic or restorative action (G. Proserpio, E. Bardi, A. M. Massera—Cosmetic Index—Sinerga Ed.).

Surprisingly, an extract of lupulus applied locally to the vaginal region has proved efficacious in reducing vaginal dryness and the disorders correlated to atrophic vaginitis, such as pruritus, burning sensation, vaginal inflammation or oedema, and dyspareunia.

The extracts of lupulus such as, for example, the dry extract, the soft extract, the fluid extract, the glycolic extract, etc. are generally obtained by using the dried plant which is subjected to extraction with suitable solvents (e.g. water, ethanol, glycerol, propylene glycol, etc.) by the use of heat; also the removal of the extraction solvent, when required (dry extract, soft extract, etc.) is carried out using heat.

It is clear that these extracts, both through the particular form of the plant material used (dried plant) and through the use of heat during the production process, undergo more or less marked changes—denaturing.

The Mother Tincture (T.M.) is the extract obtained by definition, from the fresh plant, grown in its natural habitat and gathered in its balsamic period, as rigorously defined by the Ph. Fr. VII (F. Bettiol—Manual of galenic preparations—New Techniques, ed. 1996).

The extraction process is conducted at ambient temperature and the extraction procedure is well defined by the precise indications listed in the cited French Pharmacopoeia or in the German homeopathic pharmacopoeia (*Homeopatische ArzneiBuch* 1.3 *Nachtrag-H.A.B.* 1.3).

For example, the T.M. is obtained by using the fresh cones (strobili), gathered in September-October; these are sieved to obtain lupoline, which is macerated with continuous stirring in a hydroalcoholic solution of a strength suitable for obtaining a final proof of 60°; maceration continues for 3 weeks, at the end of which filtration takes place; the liquid obtained is the T.M. (M. Rossi, loc.cit.).

It is clear that the phytocomplex present in the T.M. is that which maintains to the greatest extent the distinctive characteristics present in the fresh plant.

The compositions of the present invention are therefore particularly useful for the treatment of the manifestations of altered trophism of the mucosa and the tissue of the vagina and the vulva.

DESCRIPTION OF THE INVENTION

The subject of the present invention is the use of lupulus for the preparation of formulations for the treatment of manifestations of altered trophism of the mucosa and tissue of the vagina and the vulva.

In particular, the subject of the present invention is represented by the use of lupulus for the treatment of vaginal dryness, and of the associated disorders, such as burning sensation, pruritus, inflammation, oedema, or dyspareunia.

Preparations of lupulus, preferably semi-solid or liquid, in the form of a cream, gel, ointment, foam or vaginal wash, having a lupulus content of from 0.05 to 25 p.b.w. %, more preferably from 0.1 to 15 p.b.w. %, and even more preferably from 0.5 to 5 p.b.w. %, are efficacious for application in the vaginal and/or vulvar region, for the treatment of manifestations of altered trophism of the vaginal mucosa and of the external genitalia, such as dryness, burning sensation, pruritus, inflammation, oedema or dyspareunia.

Solid preparations of lupulus, in the shape of ovules, plugs, vaginal compresses, having a lupulus content of from 1 to 200 mg per unit dose, more preferably from 5 to 100 mg per unit dose, and even more preferably from 10 to 50 mg per unit dose, are efficacious for application to the vaginal region, for the treatment of the manifestations of altered trophism of the vaginal mucosa, such as vaginal dryness, burning sensation, pruritus, inflammation, oedema or dyspareunia.

The pharmaceutical compositions are prepared according to conventional techniques, using compatible excipients and pharmaceutically acceptable carriers, and may contain in association other active ingredients with complementary or in any case useful activity. Examples of these compositions prepared according to the present invention comprise: creams, ointments, gels, foams, washes, solutions, emulsions or suspensions, for application to the vaginal region or the external genitalia; in addition, compresses, plugs, capsules or ovules for vaginal application; forms suitable for delayed or protracted dissolution and for extended release of the active ingredient.

More precisely, the compositions prepared according to the following invention may comprise an excipient base, preferably liposomal, characterised by distinctive properties such as, for example, high moisturising activity and marked lubricating action which heighten and synergise the distinctive properties of the lupulus and of its extracts, in particular the distinctive properties of the T.M. Said excipient is normally present in an amount of between 0.01 and 15 p.b.w. %, preferably between 0.1 and 10 p.b.w. %, and even more preferably between 0.5 and 5 p.b.w. %.

The formulations of the invention which comprise a liposomal excipient base are prepared by dispersing one or more phospholipidic, sphingolipidic, glycolipidic or proteolipidic substances together with extracts of lupulus in a solvent or in an aqueous mixture of solvents. The substances cited have a liposomal transport structure plastic function, by virtue of their natural capacity for forming a double layer when hydrated.

The liposomal suspensions according to the invention may further contain, to make up to 100%, one or more of the following compounds:
1. agents modulating the gel/liquid transition temperature, such as cholesterol or its esters typical of any phospholipid;
2. ionised substances which, at the pH of the preparation, are partially or totally dissociated, therefore they act as ions capable of conferring on the liposomal surface a nett positive or negative charge. Examples of these substances are diacetylphosphate, phospholipidic acid, phosphatidyl-serine, phosphatidyl-ethanolamine, stearylamine, cardiolipine;
3. antioxidants capable of inhibiting the peroxidation of the double bonds in the fatty acids, contained in the lipidic substances. Examples of these substances are tocopherols and their esters, butylhydroxyanisol, butylhydroxytoluene and beta-carotene, ascorbic acid and its derivatives;
4. chelating agents, capable of complexing with multivalent bonds the metal ions which may act as aggregation nuclei of liposomal structures, or as catalysts for oxidative reactions;
5. hydrating agents, capable of increasing the specific activity of the liposomal system such as, for example, alcohols, polyhydroxylated glycols, mucopolysaccharides, and the like;
6. thermoviscosising and mucoadhesive agents, such as, for example, polyoxyethylene, polyoxypropylene polymer, polyoxyethylene-polyoxypropylene block copolymers (known by the commercial name of Lutrol F127);
7. decongestants such as the dry, aqueous, hydroalcoholic or hydroglycolic extracts of camomile, malva (mallow), althea (marshmallow) and the like;
8. cicatrising agents, such as extracts of *Triticum vulgare*, *Centella asiatica*, hyaluronic acid or derivatives, and the like;
9. disinfectant or antibacterial agents, such as the esters of parahydroxybenzoic acids, benzoic acid and its esters, sorbic acid and its salts, dehydroacetic acid and its salts, antimycotics such as, for example, Nystatin, Natanycin, Amphotericin, Candicidine, Mepartricine, Miconazole, Econazole, Tioconazole, Cyclopirox and their salts; antibiotics such as, for example, Chloramphenicol, Metronidazole, Nifuratel, Carphecillin, Oxytetracycline, Clindamycin, Pentamycin, etc.; anti-inflammatories such as, for example, Diclofenac, Ibuprofen, Naproxen, Flunoxaprofen, Benzydamine, etc; probiotics such as, for example, *Lactobacillus fermentum*, etc.; acidifiers such as, for example, lactic acid, acetic acid, ascorbic acid, pyrrolidone-carboxylic acid, etc; humectants such as, for example, glycerol, propylene glycol, polyglycols, etc.;
10. any other excipients, such as perfumes and essences, colorants, and the like;
11. water.

The compositions and the use of the present invention are described more clearly in, although not limited to, the following examples.

EXAMPLE 1

A formulation in gel form is prepared with the following composition in p.b.w. %:
lupulus T.M. (p.b.w.) 1%
propylene glycol 13% (p.b.w.)
Carbopol* 980 0.75%
* The term "Carbopol" is intended to mean homopolymers of acrylic acid crosslinked with polyalkenyl polyether.
soya lecithin 0.8%
cholesterol 0.20%
vitamin E acetate 0.02%
sodium hyaluronate 0.05%
sodium nipagin 0.36%
sodium nipasol 0.04%
imidazolidinilurea 0.20%
bisodium EDTA 0.10%
triethanolamine 0.2% (p.b.w.)
purified water U.P. q.s. to 100%
a) the following ingredients are dissolved: sodium nipagin 0.36%—sodium nipasol 0.04%—imidazolidinilurea 0.20%—bisodium EDTA 0.10%—sodium hyaluronate 0.05% in purified water U.P. 55% (p.b.w.)
b) the following ingredients are dissolved: vitamin E acetate 0.02%—soya lecithin 0.8%—cholesterol 0.20% in ethyl alcohol 5% (p.b.w.)
c) a) and b) are combined, and after brief agitation the ethanol is removed under reduced pressure to obtain the liposome composition. Propylene glycol 13% (p.b.w.)—lupulus T.M. (p.b.w.) 1% are added d) Carbopol 980 0.75% is dispersed in purified water U.P. 23.28%; and triethanolamine 0.2% (p.b.w.) is added to obtain the gelling of the polymer.
e) d) and c) are combined, agitating the mixture to complete homogeneity

EXAMPLE 2

A formulation in the form of a gel cream is prepared with the following composition in p.b.w. %:
lupulus T.M. (p.b.w.) 1%
propylene glycol 13% (p.b.w.)
Carbopol 980 0.75%
soya lecithin 0.8%
cholesterol 0.20%
vitamin E acetate 0.02%
sodium hyaluronate 0.025%
sodium nipagin 0.36%
sodium nipasol 0.04%
imidazolidinilurea 0.20%
bisodium EDTA 0.10%
triethanolamine 0.2% (p.b.w.)
purified water U.P. q.s. to 100%
The procedure is as in Example 1

EXAMPLE 3

A formulation is prepared in the form of a fluid cream with the following composition in p.b.w. %:
lupulus T.M. (p.b.w.) 1%
propylene glycol 13% (p.b.w.)
Carbopol 980 0.75%
soya lecithin 0.64%
cholesterol 0.16%
vitamin E acetate 0.02%
sodium hyaluronate 0.025%
sodium nipagin 0.36%
sodium nipasol 0.04%
imidazolidinilurea 0.20%
bisodium EDTA 0.10%
triethanolamine 0.2% (p.b.w.)
purified water U.P. q.s. to 100%
The procedure is as in Example 1

EXAMPLE 4

A gel based on extract of lupulus formulated as in Example 1 was studied in 10 post-menopausal women, aged between 45 and 70, having objective and subjective symptoms of urogenital atrophy. The gel was applied to the external genitalia of the 10 women at the dose of 1-2 g per day for 30 days.

During two visits, baseline and control, evaluations were made of the efficacy on the vulvo-vaginal objective symptoms (oedema, erythema, leakages, genital atrophy). The subjective urogenital symptoms (pruritus and burning sensation) were evaluated daily by the subjects and entered in a diary. The evaluations were all made according to a semi-quantitative scale from 1 (symptom absent) to 4 (maximum severity of the symptom).

The results confirmed the reduction of the frequency and the intensity of all the symptoms and a good safety profile.

EXAMPLE 5

A gel formulation prepared as in Example 1 was studied in 100 adult women affected by vaginal dryness and other disorders correlated to genital atrophy. Each woman applied the product deeply in the vagina, by means of a cannula, at a rate of 2.5 g of gel per day for one week, followed by 2 applications per week for another 11 weeks. The primary parameter of efficacy consisted of the evaluation of vaginal dryness evaluated by means of a visual analog scale (VAS). The secondary parameters comprised the evaluation of all the other objective and subjective associated symptoms (pruritus, burning sensation, dyspareunia, vaginal inflammation/oedema and eruptions) evaluated by means of a 4-point scale, and also the presence of vaginal abrasions and disepithelialisation.

Figure 1:
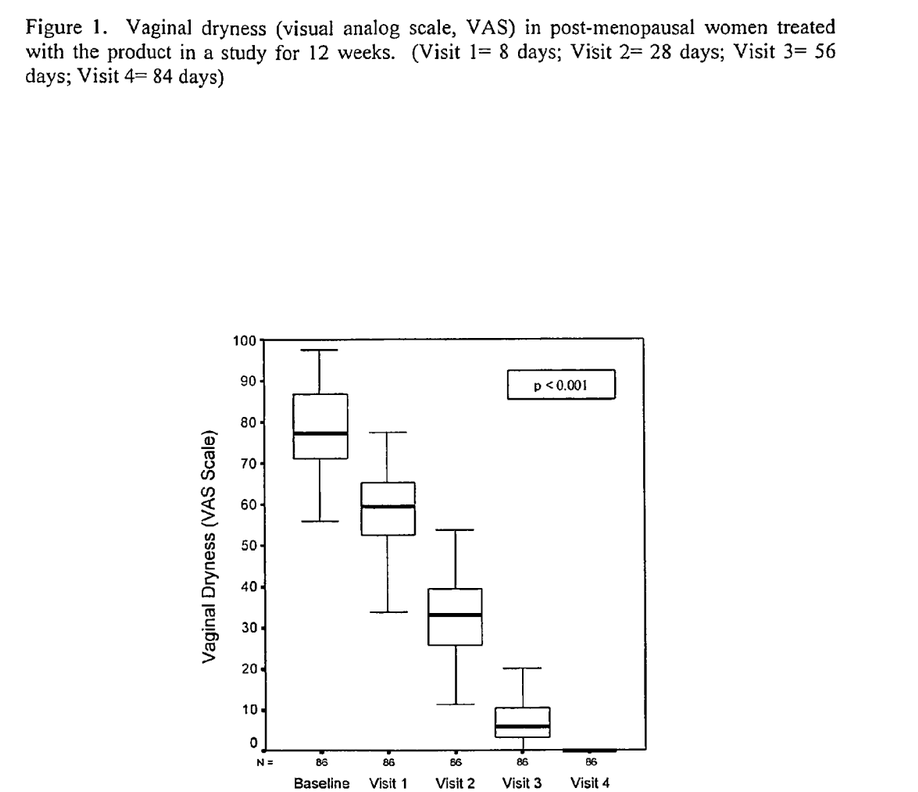
FIG. 1. Vaginal dryness (visual analog scale, VAS) in post-menopausal women treated with the product in a study for 12 weeks. (Visit 1=8 days; Visit 2=28 days; Visit 3=56 days; Visit 4=84 days).
Figure 2:
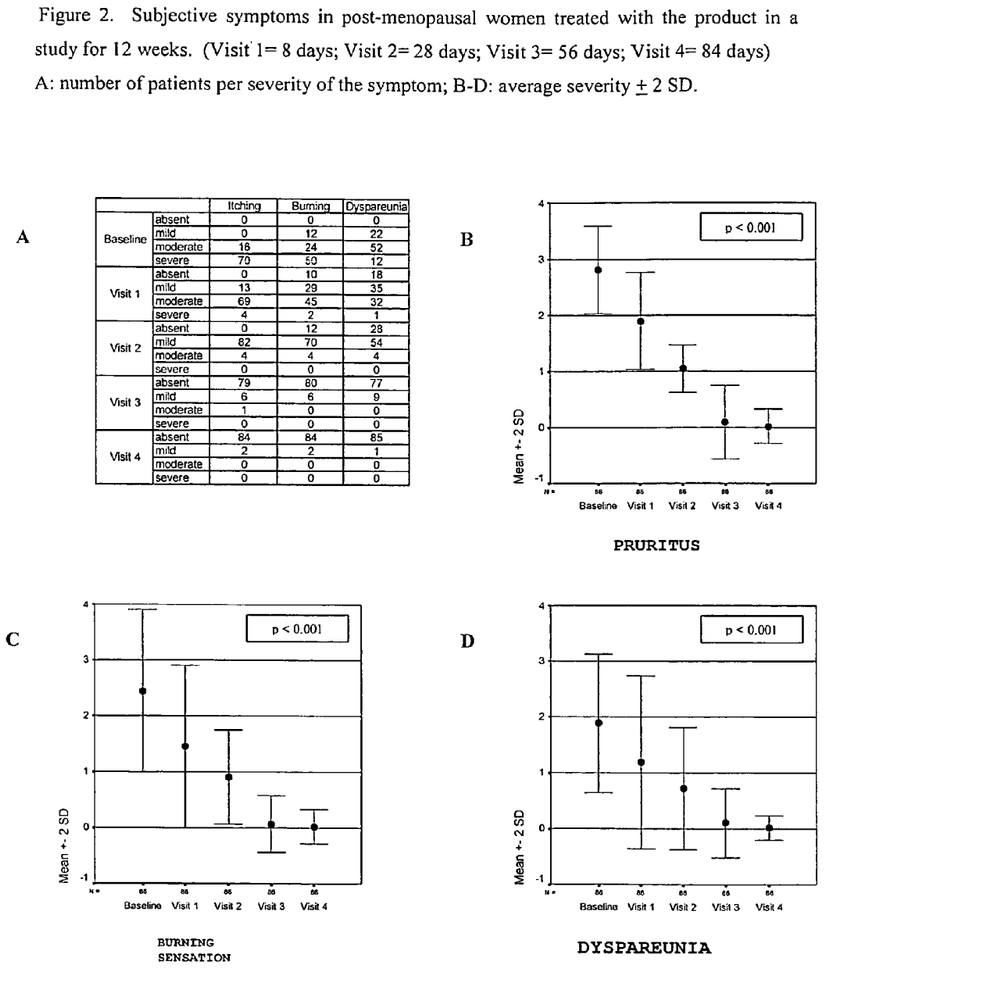
FIG. 2. Subjective symptoms in post-menopausal women treated with the product in a study for 12 weeks. (Visit 1=8 days; Visit 2=28 days; Visit 3=56 days; Visit 4=84 days). A: number of patients per severity of the symptom; B-D: average severity +2 SD.
Figure 3:
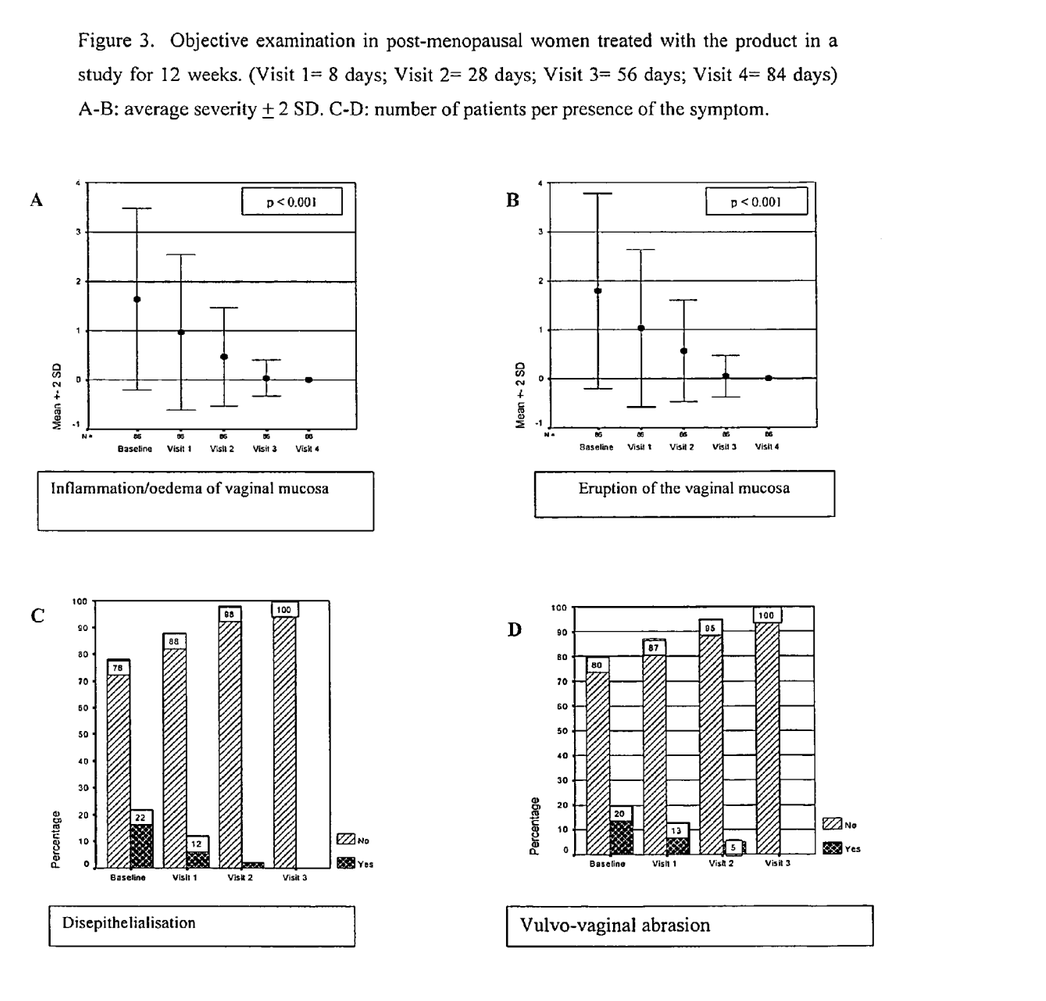
FIG. 3. Objective examination in post-menopausal women treated with the product in a study for 12 weeks. (Visit 1=8 days; Visit 2=28 days; Visit 3=56 days; Visit 4=84 days) A-B: average severity +2 SD. C-D: number of patients per presence of the symptom.

The results are shown in FIGS. 1-3.

The results show a marked effect of the product studied both on vaginal dryness, and on the other symptoms, which were reduced in a statistically significant manner starting from the first week of treatment, without exhibiting undesirable side effects.

EXAMPLE 6

In order to verify whether the compound as per the Example 1 is active through an estrogenic stimulation of the vaginal epithelium, this has been compared to an estrogenic gel formulation in an in vitro proliferation test of vaginal epithelium cells.

The formulation of test product was equal to the formulation of Example 1 (called Gynomunal® in this investigation)

As reference formulation, it has been used the compound Gelestra®, commercially available on the Italian market, with the following composition for a 2.5 g sachet as declared by the Manufacturer:
active principle: estradiol 1.5 mg; other ingredients: ethylalcohol, methylparaben, propylparaben, carbopol, triethanolamine, purified water. Gelestra® is indicated in the treatment of symptoms due to menopause-induced estrogenic deficiency.

Cell Culture Method:

Vaginal cell line HeLa (Human Negroid cervix epitheloid carcinoma) (ECACC n. 93021013) has been allowed to proliferate in plastic flasks in 20 ml of Minimum Essential medium Eagle (EMEM) containing 1% v/v of a solution penicillin-streptomycin 100× (pen/strep), 1% v/v of glutamin 2 mM, 1% v/v of non essential aminoacids and stored into a 5% CO2 Incubator at 37° C. After 5 days, the obtained tissue on the flask bottom has been washed with "Dulbecco's Phosphate Buffered Saline" (PBS) and treated with 1 ml of trypsin-EDTA 2000× solution to re-suspend cells. Cell culture has been incubated for 2 min. After inactivation of trypsin, cell suspension has been centrifuged at 1000 rpm for 10 min and re-suspended in the same medium.

Evaluation of Cell Proliferation Induction of Gelestra® and Gynomunal

Gelestra® and the test product as per the Example 1 have been diluted in a medium prepared as previously described, in order to obtain an estradiol concentration of $10^{-6}$M (Gelestra®). 200 µl of samples have been in contact with cells for 24 hours. 200 µl of Neutral Red (NR) 0.33 mg/ml (Tox Kit 4, Sigma-Aldrich,) has been added. After 2 hours, cells have been washed and treated with a CaCl2 1% w/v and formaldehyde 0.5% w/v solution. Lysosome membranes have been broken by using 200 µl of a 1% w/v CH3COOH ethanol 50% v/v solution. Absorbance has been recorded at 490 nm with a 650 nm filter by using a ELISA plate reader.

Figure 4:
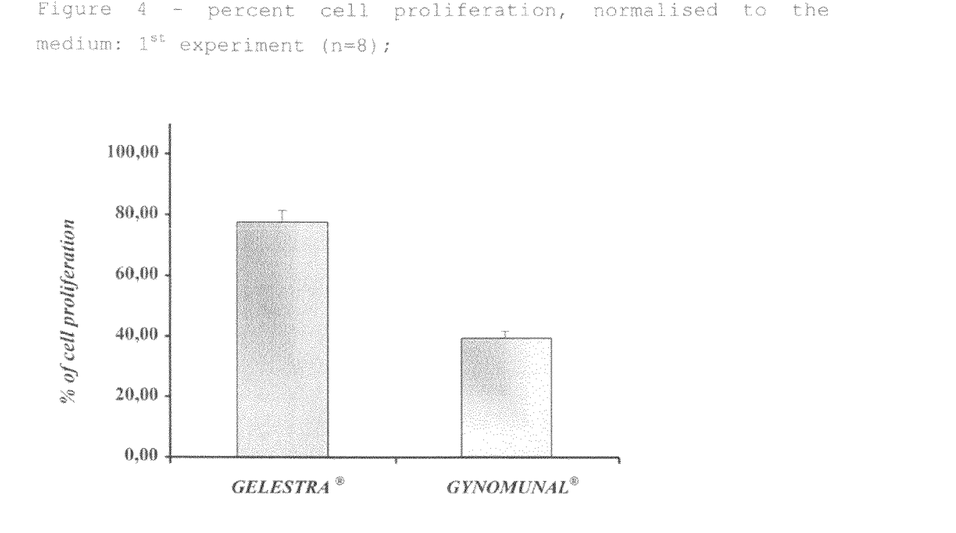
FIG. 4—percent cell proliferation, normalised to the medium: $1^{st}$ experiment (n=8).
Figure 5:
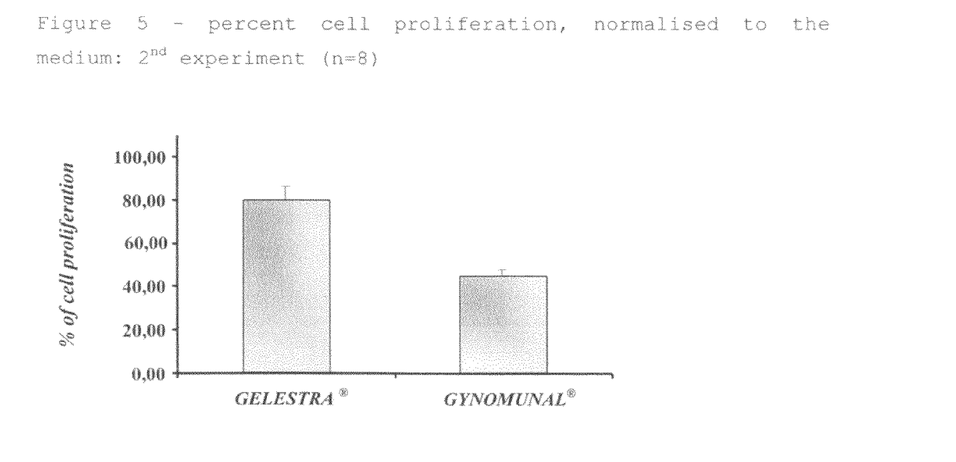
FIG. 5—percent cell proliferation, normalised to the medium: 2nd experiment (n=8).
Figure 6:
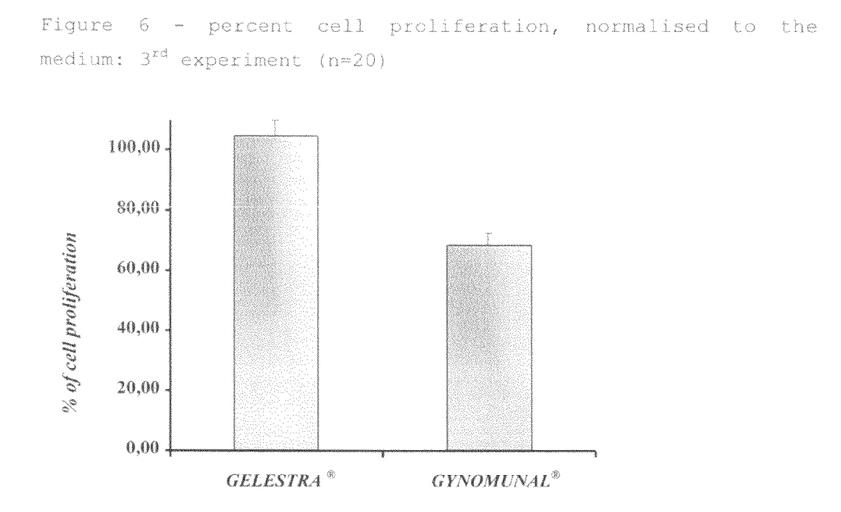
FIG. 6—percent cell proliferation, normalised to the medium: 3rd experiment (n=20).

Evaluation of both test and reference performances is shown in FIG. (4-6) as % of cell proliferation, normalised to the medium and as an average of experiments performed during 3 different days.

Results:

The proliferation of vaginal cells induced by the test product as per the Example 1 is very low and significantly lower than that induced by the reference Gelestra® due to the presence of estrogens in the latter composition (Mann Whitney test, $p<0.01$ for all experiments).

Thus, it is concluded that the test product as per the Example 1 does not show any estrogenic effect in this model.

The invention claimed is:

1. A method of treating a living animal body afflicted with a condition selected from atrophic vulvo-vaginitis, vaginal dryness and disorders related thereto, comprising the step of applying topically to the vaginal and/or vulvar region of the living animal body a formulation comprising between 1 and 15 weight percent *Humulus lupulus* Mother Tincture obtained from a hydroalcoholic extract of a fresh *Humulus lupulus* plant or a hydroalcoholic macerate of the fresh *Humulus lupulus* plant, wherein the *Humulus lupulus* formulation does not exhibit an estrogenic effect, and wherein the estrogenic effect is vaginal cell proliferation, and is effective for treatment of the condition.

2. The method of claim 1, wherein the related conditions are selected from pruritus, burning sensation, dryness, and changes in the trophism of the vulvar and/or vaginal tissue and/or mucosa.

3. The method of claim 1, wherein formulation comprises between 0.5 and 5% 1 and 5 weight percent *Humulus lupulus* Mother Tincture.

4. The method of claim 1, wherein the formulation is in the form of a cream, gel, wash, ointment, foam, solution, emulsion or suspension.

5. The method of claim 1, wherein the formulation comprises of at least one pharmacologically acceptable excipient.

6. The method of claim 5, wherein the excipient is a liposomal excipient.

7. The method of claim 6, wherein the liposomal excipient comprises one or more phospholipid, sphingolipid, glycolipid, proteolipid or aqueous phase.

8. The method of claim 5, wherein the formulation comprises between 0.01 and 15% weight percent excipient.

9. The method of claim 8, wherein the formulation comprises between 0.1 and 10% weight percent excipient.

10. The method of claim 9, wherein the formulation comprises between 0.5 and 5% weight percent excipient.

11. The method of claim 1, wherein said formulation comprises one or more constituents selected from cholesterol and its esters; ionising agents; antioxidants; chelating agents; hydrating agents; thermoviscosizing agents; decongestants; disinfectants and/or antibacterial agents; perfumes; essences and colorants.

12. The method of claim 1, wherein the formulation comprises at least one polymer.

13. The method of claim 12, wherein the polymer has a thermoviscosizing effect.

14. The method of claim 13, wherein said polymer is selected from homopolymers of acrylic acid crosslinked with polyalkenyl polyether, polyoxyethylene-polyoxypropylene block copolymers, cellulose or acrylic derivatives, alginates, collagen, hyaluronic acid or its derivatives, and chitosan or its derivatives.

15. The method of claim 1, wherein the formulation contains hydrating agents selected from alcohols, polyhydroxylated glycols, mucopolysaccharides, lactic acid or its salts, 2-pyrrolidone-carboxylic acid or its salts, vegetable or mineral oils, and silicones and derivatives.

16. The method of claim 1, wherein the formulation comprises ethanol and/or other pharmacologically acceptable solvents.

* * * * *

UNITED STATES PATENT AND TRADEMARK OFFICE
CERTIFICATE OF CORRECTION

PATENT NO. : 9,011,902 B2
APPLICATION NO. : 12/220160
DATED : April 21, 2015
INVENTOR(S) : Michele Di Schiena

Page 1 of 1

It is certified that error appears in the above-identified patent and that said Letters Patent is hereby corrected as shown below:

Title Page, Item (56), Foreign Patent Documents: "JP 2004537804" should be
--JP   2004537604--.

Title Page, Item (56), Foreign Patent Documents: "JP 2005323873   12/2008" should be
--JP 2005323873   12/2005--.

Signed and Sealed this
Eighteenth Day of August, 2015

Michelle K. Lee
*Director of the United States Patent and Trademark Office*